(12) United States Patent
Wang et al.

(10) Patent No.: US 7,838,677 B2
(45) Date of Patent: Nov. 23, 2010

(54) PROCESSES FOR PREPARING MORPHINANS AND INTERMEDIATES THEREOF

(75) Inventors: Peter Xianqi Wang, Chesterfield, MO (US); Frank W. Moser, Arnold, MO (US); Gary L. Cantrell, Troy, IL (US); Jian Bao, Chesterfield, MO (US)

(73) Assignee: Mallinckrodt Inc, Hazelwood, MO (US)

( * ) Notice: Subject to any disclaimer, the term of this patent is extended or adjusted under 35 U.S.C. 154(b) by 670 days.

(21) Appl. No.: 11/908,136

(22) PCT Filed: Feb. 23, 2006

(86) PCT No.: PCT/US2006/006285

§ 371 (c)(1),
(2), (4) Date: Sep. 10, 2007

(87) PCT Pub. No.: WO2006/098855

PCT Pub. Date: Sep. 21, 2006

(65) Prior Publication Data

US 2008/0262231 A1 Oct. 23, 2008

Related U.S. Application Data

(60) Provisional application No. 60/660,241, filed on Mar. 10, 2005.

(51) Int. Cl.
C07D 221/22 (2006.01)
C07D 489/02 (2006.01)

(52) U.S. Cl. .............................. 546/74; 546/44; 546/149

(58) Field of Classification Search .................... 546/74, 546/44, 149
See application file for complete search history.

(56) References Cited

U.S. PATENT DOCUMENTS

| 2,634,292 | A | 4/1953 | Hellerbach |
| 2,638,472 | A | 5/1953 | Grewe |
| 2,723,268 | A | 11/1955 | Henecka |
| 2,769,810 | A | 11/1956 | Ochiai et al. |
| 3,914,234 | A | 10/1975 | Mohacsi et al. |
| 3,919,237 | A | 11/1975 | Halder |
| 4,003,903 | A | 1/1977 | Schwartz |
| 4,058,531 | A | 11/1977 | Monkovic et al. |
| 4,368,326 | A | 1/1983 | Rice |
| 4,405,626 | A | 9/1983 | Johnson |
| 4,410,700 | A | 10/1983 | Rice |
| 4,514,569 | A | 4/1985 | Hendrickson et al. |
| 4,521,601 | A | 6/1985 | Rice |
| 4,556,712 | A | 12/1985 | Rice |
| 4,613,668 | A | 9/1986 | Rice |
| 4,727,146 | A | 2/1988 | Rice |
| 2003/0036550 | A1 | 2/2003 | Fedler et al. |

FOREIGN PATENT DOCUMENTS

| EP | 0 155 424 | 9/1985 |
| FR | 2784986 | 4/2000 |
| GB | 1055478 | 1/1967 |
| WO | WO 2004/031204 | 4/2004 |

OTHER PUBLICATIONS

Rice, "Synthetic opium alkaloids and derivatives. A short total synte\hesis of (+−)-dihydrothebainone, (+−_-dihydrocodeinone, and (+−)-nordihydrocodeinone as an approach to a practical synthesis of morphine, codeine, and congeners", Journal of Organic chemistry, 1980, vol. 45, No. 15, pp. 3135-3137, XP002396231.

Rao et al., "11Beta-substituted 13beta-ethyl gonane derivatives exhibit reversal of antiprogestational activity" Steroids, 1998, vol. 63, No. 1, pp. 50-57, XP002396232.

Passarella et al., A Convenient Synthesis of $\Delta^{7,8}$-Morphinan-6-one and Its Direct Oxidation to 14-Hydroxy- $\Delta^{7,8}$-morphinan-6-one, Bioorganic & Medicinal Chemistry Letters 12 (2002) 1981-1983.

*Primary Examiner*—Charanjit S Aulakh

(57) ABSTRACT

The present invention is directed to processes for the synthesis of morphinans. In particular, a process for cyclizing a $\beta,\gamma$-bicyclic ketone compound to form a nordihydrothebainone product using the Grewe cyclization reaction is improved by forming a reaction mixture comprising a $\beta,\gamma$-bicyclic ketone compound, a cyclizing acid and a water scavenging cyclization additive. In one embodiment, the Grewe transformation occurs in the presence of an acid anhydride as the cyclization additive. Further, the present invention is directed to processes for converting $\alpha,\beta$-bicyclic ketone compounds (e.g., by-products of the Grewe cyclization reaction) to $\beta,\gamma$-bicyclic ketone compounds, wherein the $\beta,\gamma$-bicyclic ketone compounds may be recovered to further undergo Grewe cyclization and form the nordihydrothebainone product.

14 Claims, No Drawings

PROCESSES FOR PREPARING MORPHINANS AND INTERMEDIATES THEREOF

CROSS REFERENCE TO RELATED APPLICATIONS

This application is a national stage application of PCT/US2006/006285, filed 23 Feb. 2006, which claims the benefit of U.S. Provisional Application No. 60/660,241 filed 10 Mar. 2005.

BACKGROUND OF THE INVENTION

The present invention is generally directed to processes for the synthesis of morphinans, more specifically, nordihydrothebainone and its analogs.

Nordihydrothebainone and its derivatives are important synthetic intermediates to many morphinan compounds including burprenorphine, codeine, etorphine, hydrocodone, hydromorphone, morphine, nalbuphine, nalmefene, naloxone, naltrexone, oxycodone, and oxymorphone. Generally, these compounds are analgesics, which are used extensively for pain relief in the field of medicine due to their action as opiate receptor agonists. However, nalmefene, naloxone and naltrexone are opiate receptor antagonists; and are used for reversal of narcotic/respiratory depression due to opiate receptor agonists.

Various processes for the synthesis of nordihydrothebainone and its analogs are known. Generally, a Grewe cyclization reaction is used to obtain nordihydrothebainone. In U.S. Pat. No. 4,368,326, Rice discloses a process of preparing a nordihydrothebainone (e.g., 1-bromo-N-formylnordihydrothebainone) from a β,γ-hexahydroisoquinolinone (e.g., 1-(2'-bromo-4'-methoxy-5'-hydroxybenzyl)-2-formyl-1,3,4,5,7,8-hexahydroisoquinolin-6-one) by Grewe cyclization catalyzed using a super acid catalyst alone or with a combination of an ammonium fluoride complex and trifluoromethanesulfonic acid.

Contaminants in the starting β,γ-hexahydroisoquinolinone used in the Grewe cyclization cause reproducibility problems and low yields of the desired cyclized product. One known method for increasing the reproducibility and yield of the Grewe cyclization step is to purify the starting β,γ-hexahydroisoquinolinone by crystallization. However, crystallization of the β,γ-hexahydroisoquinolinone is difficult since it typically consists of a mixture of rotational isomers. In addition, α,β-hexahydroisoquinolinones are isomeric by-products of the Grewe cyclization of β,γ-hexahydroisoquinolinones. Under conventional conditions, the α,β-hexahydroisoquinolinone does not undergo the Grewe cyclization reaction to an appreciable extent to form the desired nordihydrothebainone product. Accordingly, known Grewe cyclization conditions often produce low yields of the nordihydrothebainone product due to a significant amount of the β,γ-hexahydroisoquinolinone starting material being converted into α,β-hexahydroisoquinolinones.

The presence of water is one factor that affects the reproducibility and yield of the Grewe cyclization reaction. Water in the reaction mixture may reduce selectivity by contributing to the conversion of the β,γ-hexahydroisoquinolinone starting material into undesirable α,β-hexahydroisoquinolinones. Water may be introduced into the Grewe cyclization reaction medium from the starting β,γ-hexahydroisoquinolinone and the cyclizing acid reagents used. Generally, commercially available acids used to catalyze the Grewe cyclization have a measurable amount of water present because of their hygroscopic nature. Other contaminants known to affect the yield of the Grewe cyclization reaction are alcohols and organic acids.

The undesirable α,β-hexahydroisoquinolinone isomer by-products produced during the Grewe cyclization reaction can be difficult to separate and once separated are typically discarded. This practice results in a significant loss in productivity and efficiency due to the many steps necessary to synthesize the starting β,γ-hexahydroisoquinolinone; for example, starting with 3-methoxyphenethylamine as described by Rice in U.S. Pat. No. 4,368,326. Being able to regenerate the β,γ-hexahydroisoquinolinone starting material would significantly reduce the amount of wasted material, capital equipment, labor, and improve overall yield in the synthesis of nordihydrothebainone products.

Thus, a need persists for processes for the synthesis of nordihydrothebainone and analogs thereof including Grewe cyclization capable of inhibiting by-product formation and increasing yields.

SUMMARY OF THE INVENTION

Among the various aspects of the present invention are improved processes for the synthesis of intermediates (e.g., nordihydrothebainones converted from the corresponding β,γ-bicyclic ketones) useful in the preparation of various morphinan compounds.

One aspect of the present invention is a process for the preparation of a nordihydrothebainone product comprising nordihydrothebainone or an analog thereof having the structure of formula 10:

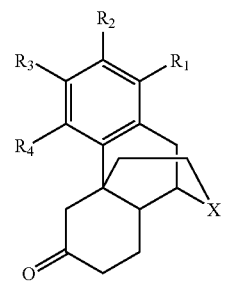

wherein
X is selected from the group consisting of oxygen, sulfur, —S(O)—, —S(O$_2$)—, —C(R$_{18}$R$_{19}$)—, —N(R$_{17}$)— and —N$^+$(R$_{17a}$R$_{17b}$)—; R$_1$, R$_2$, R$_3$, R$_4$, R$_{18}$, and R$_{19}$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro, or R$_{18}$ and R$_{19}$ together form keto; R$_{17}$ is selected from the group consisting of hydrogen, acyl, alkenyl, alkoxyaryl, alkyl, alkynyl, aryl, carboxyalkenyl, carboxyalkyl, cyanoalkyl, cycloalkyl, cycloalkylalkyl, haloalkyl, heteroaryl, heterocyclic, carboxyl, carboxyamide, carboxyester, hydroxyl and hydroxyalkyl; and R$_{17a}$ and R$_{17b}$ are independently selected from the group consisting of hydrogen, alkyl, cycloalkyl, cycloalkylalkyl, aryl and benzyl or together form oxo. The process comprises: forming a reaction mixture comprising a β,γ-bicyclic ketone compound, a cyclizing acid and an acid anhydride to produce the nordihydrothebainone product, the β,γ-bicyclic ketone compound having the structure of formula 11:

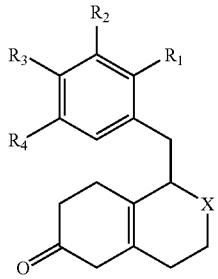

wherein

X, $R_1$, $R_2$, $R_3$, $R_4$, $R_{17}$, $R_{18}$ and $R_{19}$ and are as defined above.

Another aspect of the present invention is a process for the preparation of nordihydrothebainone or an analog thereof having the structure of formula 10:

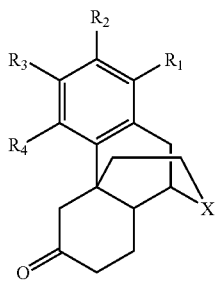

wherein

X is selected from the group consisting of oxygen, sulfur, —S(O)—, —S(O$_2$)—, —C($R_{18}R_{19}$)—, —N($R_{17}$)— and —N$^+$($R_{17a}R_{17b}$)—; $R_1$, $R_2$, $R_3$, $R_4$, $R_{10}$, and $R_{19}$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro, or $R_{18}$ and $R_{19}$ together form keto; $R_{17}$ is selected from the group consisting of hydrogen, acyl, alkenyl, alkoxyaryl, alkyl, alkynyl, aryl, carboxyalkenyl, carboxyalkyl, cyanoalkyl, cycloalkyl, cycloalkylalkyl, haloalkyl, heteroaryl, heterocyclic, carboxyl, carboxyamide, carboxyester, hydroxyl and hydroxyalkyl; and $R_{17a}$ and $R_{17b}$ are independently selected from the group consisting of hydrogen, alkyl, cycloalkyl, cycloalkylalkyl, aryl and benzyl or together form oxo. The process comprises: contacting a β,γ-bicyclic ketone compound with a cyclizing acid in the presence of an acid anhydride, the β,γ-bicyclic ketone compound having the structure of formula 11:

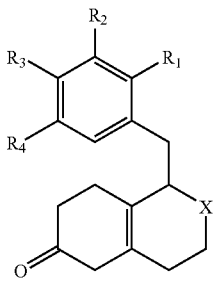

wherein

X, $R_1$, $R_2$, $R_3$, $R_4$, $R_{17}$, $R_{18}$ and $R_{19}$ and are as defined above.

Yet another aspect of the present invention is a process for the preparation of a β,γ-bicyclic ketone compound having the structure of formula 20:

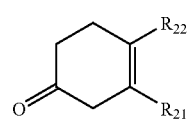

wherein $R_{21}$ and $R_{22}$ together with the carbons to which they are attached form a 5-, 6- or 7-membered heterocyclic or carbocyclic ring fused to the cyclohexene ring. The process comprises: reacting an α,β-bicyclic ketone compound with a ketone protecting compound to form a protected β,γ-bicyclic ketone compound and hydrolyzing the protected β,γ-bicyclic ketone compound to produce the β,γ-bicyclic ketone compound; the α,β-bicyclic ketone compound having the structure of formulae 21 or 22 and the protected β,γ-bicyclic ketone compound having the structure of formula 23:

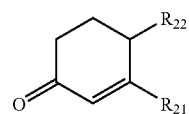

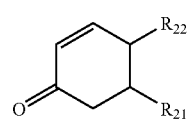

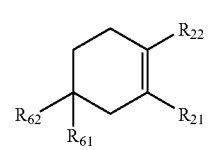

wherein $R_{21}$ and $R_{22}$ are as defined above; and $R_{61}$ and $R_{62}$ are independently selected from the group consisting of alkoxy and alkylthio or together with the carbons to which they are attached form a ketal, dithioketal or monothioketal.

A further aspect of the present invention is a process for the preparation of a nordihydrothebainone product comprising nordihydrothebainone or an analog thereof having structure of formula 10:

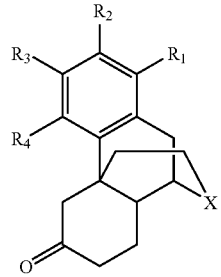

10 wherein

X is selected from the group consisting of oxygen, sulfur, —S(O)—, —S(O$_2$)—, —C(R$_{18}$R$_{19}$)—, —N(R$_{17}$)— and —N$^+$(R$_{17a}$R$_{17b}$)—; R$_1$, R$_2$, R$_3$, R$_4$, R$_{18}$, and R$_{19}$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro, or R$_{18}$ and R$_{19}$ together form keto; R$_{17}$ is selected from the group consisting of hydrogen, acyl, alkenyl, alkoxyaryl, alkyl, alkynyl, aryl, carboxyalkenyl, carboxyalkyl, cyanoalkyl, cycloalkyl, cycloalkylalkyl, haloalkyl, heteroaryl, heterocyclic, carboxyl, carboxyamide, carboxyester, hydroxyl and hydroxyalkyl; and R$_{17a}$ and R$_{17b}$ are independently selected from the group consisting of hydrogen, alkyl, cycloalkyl, cycloalkylalkyl, aryl and benzyl or together form oxo. The process comprises: (i) forming a reaction mixture comprising a β,γ-bicyclic ketone compound and a cyclizing acid in a Grewe reaction zone to produce a Grewe product mixture comprising the nordihydrothebainone product and an α,β-bicyclic ketone compound by-product, the β,γ-bicyclic ketone compound having the structure of formula 11:

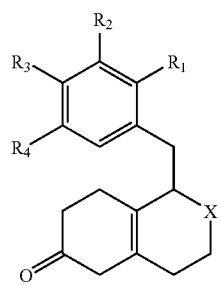

11 wherein

X, R$_1$, R$_2$, R$_3$, R$_4$, R$_{17}$, R$_{18}$ and R$_{19}$ and are as defined above; (ii) reacting the α,β-bicyclic ketone compound by-product obtained in the Grewe product mixture with a ketone protecting compound in an isomerization reaction zone to form a protected β,γ-bicyclic ketone compound, the α,β-bicyclic ketone compound by-product having the structure of formulae 30 or 31 and the protected β,γ-bicyclic ketone compound having the structure of formula 32:

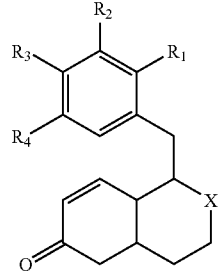

30

31

32 wherein

R$_{61}$ and R$_{62}$ are independently selected from the group consisting of alkoxy and alkylthio or together with the carbons to which they are attached form a ketal, dithioketal or monothioketal; and X, R$_1$, R$_2$, R$_3$, R$_4$, R$_{17}$, R$_{18}$ and R$_{19}$ are as defined above; and (iii) hydrolyzing the protected β,γ-bicyclic ketone compound to form the β,γ-bicyclic ketone compound of formula 11.

DETAILED DESCRIPTION OF THE PREFERRED EMBODIMENTS

Among the various aspects of the present invention is a process for preparing nordihydrothebainone and analogs thereof from β,γ-bicyclic ketone compounds (e.g., β,γ-hexahydroisoquinolinones) by an improved Grewe cyclization reaction. In one embodiment, a Grewe cyclization reaction mixture comprising a β,γ-bicyclic ketone compound, a cyclizing acid and an acid anhydride is formed. For example, the Grewe transformation of the β,γ-bicyclic ketone compound may be effected in the presence of a cyclizing acid and an acid anhydride. Generally, use of an anhydride in accordance with the present invention improves the yield of the nordihydrothebainone product.

Without being bound by theory, it is believed that addition of an anhydride to the Grewe reaction mixture may have one or more of the following effects. First, the anhydride can reduce the concentration of water in the Grewe reaction mixture that might otherwise lead to undesired specific side reactions and reduce yield of the desired nordihydrothebainone product and/or affect the acidity of the Grewe reaction medium. If the anhydride affects the acidity of the Grewe cyclization reaction medium, it may do so to favor producing the nordihydrothebainone product. Second, the anhydride may coordinate or associate in some manner to the functional groups of the β,γ-bicyclic ketone compound starting material to facilitate production of the cyclized product. Third, the anhydride may react with or otherwise affect the properties of the other impurities in the Grewe cyclization reaction mixture.

More particularly, the addition of an anhydride has been found to significantly reduce the formation of polymer side products and minimize the formation of α,β-bicyclic ketone by-products (e.g., α,β-hexahydroisoquinolinones). The α,β-bicyclic ketone by-products are formed from the acid catalyzed double bond migration of the β,γ-bicyclic ketone starting material subjected to the conditions of the Grewe transformation and do not undergo Grewe cyclization to an appreciable extent to produce the desired nordihydrothebainone product. Thus, formation of α,β-bicyclic ketone compounds reduces the yield and efficiency of the Grewe cyclization reaction.

Regardless of whether an anhydride is employed, some formation of the α,β-bicyclic ketone by-products is typically unavoidable in conducting the Grewe cyclization reaction. In accordance with another embodiment of the invention and in order to improve the overall efficiency of the transformation of the β,γ-bicyclic ketone compound to the desired nordihydrothebainone product by Grewe cyclization, α,β-bicyclic ketone by-products are isomerized back to the desired starting β,γ-bicyclic ketone compound. The reverse isomerization is generally carried out by protecting the α,β-bicyclic ketone compound with a ketone protecting compound, which causes the double bond to shift from the α,β-position to the desired β,γ-position and form a protected β,γ-bicyclic ketone compound. The protected β,γ-bicyclic ketone compound is then hydrolyzed to produce the starting β,γ-bicyclic ketone compound that can then be recycled and converted to the desired nordihydrothebainone product by the Grewe cyclization reaction.

Grewe Cyclization

The Grewe cyclization reaction is an important synthetic step in the preparation of morphinans and analogs thereof. General reaction schemes for the preparation of morphinans are disclosed in U.S. Pat. No. 4,368,326 (Rice), the entire disclosure of which is incorporated herein by reference. The morphinans and analogs thereof (i.e., the morphinans contain an X group of —N($R_{17}$)— or —$N^+$($R_{17a}R_{17b}$)— and morphinan analogs contain an X group other than —N($R_{17}$)— or —$N^+$($R_{17a}R_{17b}$)—) of interest in the practice of the present invention are opiate receptor agonists or antagonists and generally are compounds having the structure of formula 1:

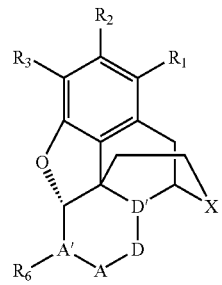

wherein
-A'-A- represents the group

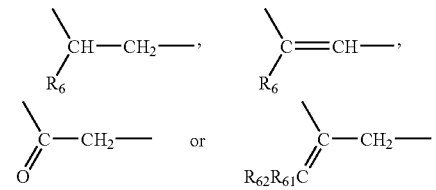

-D-D'- represents the group

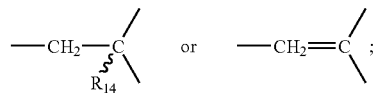

-A-D- represents the group —$CH_2CH_2$— or —CH=CH— or =CH—CH=;

X is selected from the group consisting of oxygen, sulfur, —S(O)—, —S($O_2$)—, —C($R_{18}R_{19}$)—, —N($R_{17}$)— and —$N^+$($R_{17a}R_{17b}$)—;

$R_1$ and $R_2$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro;

$R_3$ is selected from the group consisting of alkoxy, hydroxyl and acetoxy;

$R_6$ is selected from the group consisting of alkoxy, hydroxyl and acetoxy;

$R_{14}$ is selected from the group consisting of hydrogen, hydroxyl and acetoxy;

$R_{17}$ is selected from the group consisting of lower alkyl, alkylenecycloalkyl, allyl alkenyl, acyl, formyl, formyl ester, formamide and benzyl;

$R_{17a}$ and $R_{17b}$ are independently selected from the group consisting of hydrogen, alkyl, cycloalkyl, cycloalkylalkyl, aryl and benzyl;

$R_{18}$, and $R_{19}$ are independently selected from the group consisting of hydrogen, substituted and unsubstituted acyl, alkenyl, alkoxy, alkoxyaryl, alkyl, alkylamino, arylthio, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, halo, haloalkoxy, haloalkyl, heteroaryl, heterocyclic, hydroxyalkyl, hydroxyl and nitro or $R_{18}$ and $R_{19}$ together form keto; and $R_{61}$ and $R_{62}$ are independently selected from hydrogen, alkyl, alkenyl, alkynyl, allyl, and aryl;

provided that if -A-D- is —CH=CH—, then -A'-A- is other than —C($R_6$)=CH— and -D-D'- is other than

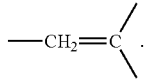

In one presently preferred embodiment, the present invention is useful in the preparation of a morphinan compound of formula 1 wherein X is —N($R_{17}$)—.

The improvements in the Grewe cyclization reaction in accordance with the present invention can be used in transforming β,γ-bicyclic ketones into nordihydrothebainone products. Techniques for transformation of β,γ-bicyclic ketones by Grewe cyclization to form nordihydrothebainone products are known in the art (See, for example, U.S. Pat. Nos. 4,368,326, 4,410,700, 4,521,601, 4,556,712, 4,613,668, and 4,727,146, the entire disclosure of which are incorporated herein by reference) and such conventional practices are generally applicable in carrying out the present invention with the modifications as set forth in detail below.

The products of the processes detailed below can be converted to the compounds of formula 1 by methods known in the art. For example, the nordihydrothebainone products or analogs thereof can be converted to morphinan compounds including burprenorphine, codeine, etorphine, hydrocodone, hydromorphone, morphine, nalbuphine, nalmefene, naloxone, naltrexone, oxycodone, and oxymorphone.

In one embodiment, the process of the present invention is directed to the preparation of nordihydrothebainone or an analog thereof having the structure of formula 10:

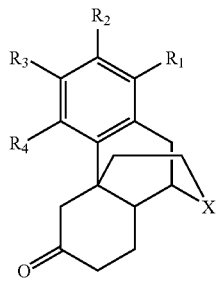

wherein

X is selected from the group consisting of oxygen, sulfur, —S(O)—, —S($O_2$)—, —C($R_{18}R_{19}$), —N($R_{17}$)— and —$N^+$($R_{17a}R_{17b}$)—;

$R_1$, $R_2$, $R_3$, $R_4$, $R_{18}$, and $R_{19}$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro, or $R_{18}$ and $R_{19}$ together form keto;

$R_{17}$ is selected from the group consisting of hydrogen, acyl, alkenyl, allyl, alkoxyaryl, alkyl, alkynyl, aryl, carboxyalk-
enyl, carboxyalkyl, cyanoalkyl, cycloalkyl, cycloalkylalkyl, haloalkyl, heteroaryl, heterocyclic, carboxyl, carboxyamide, carboxyester, hydroxyl and hydroxyalkyl; and $R_{17a}$ and $R_{17b}$ are independently selected from the group consisting of hydrogen, alkyl, cycloalkyl, cycloalkylalkyl, aryl and benzyl or together form oxo.

When $R_{17}$ is hydrogen, salts of the secondary amine can be formed wherein the anion is selected from the group consisting of chloride, bromide, acetate, formate, sulfate, bisulfate, triflate, trifluoroacetate, methanesulfonate, and the like. When X is —$N^+$($R_{17a}R_{17b}$)—, the counter-ion can be chloride, bromide, iodide, trifluoroacetate, trifluoromethanesulfonate, methanesulfonate, acetate, p-toluenesulfonate, sulfate, bisulfate, phosphate, hydrogenphosphate, dihydrogenphosphate, fumarate, malonate, oxalate, formate, tartrate, benzoate, and the like.

The process generally comprises forming a Grewe cyclization reaction mixture comprising a cyclizing acid and a β,γ-bicyclic ketone compound having the structure of formula 11:

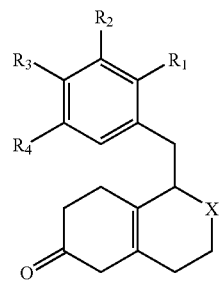

wherein

X, $R_1$, $R_2$, $R_3$, $R_4$, $R_{17}$, $R_{18}$ and $R_{19}$ and are as defined above. In one preferred embodiment, when the β,γ-bicyclic ketone starting material and nordihydrothebainone product correspond to formulae 11 and 10, respectively, $R_1$, $R_2$, $R_3$ and $R_4$ are independently halo, hydrogen, hydroxy, or methoxy and X is —N($R_{17}$)—. In a more preferred embodiment, $R_4$ is hydroxy, $R_3$ is methoxy or hydroxy, $R_2$ is hydrogen, $R_1$ is bromine or chlorine, X is —N($R_{17}$)—, and $R_{17}$ is formyl or hydrogen or X is —$N^+$($R_{17a}R_{17b}$)— and $R_{17a}$ and $R_{17b}$ are hydrogen.

In a particularly preferred embodiment, the norhydrothebainone product has the structure of formula 10A and the β,γ-bicyclic ketone starting material has the structure of formula 11A:

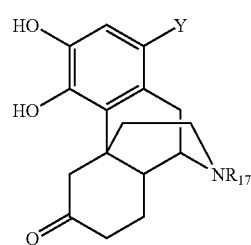

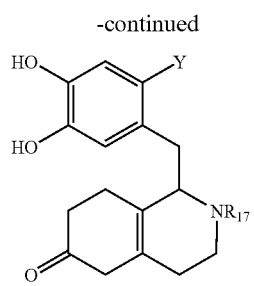

wherein

Y is a F or Cl; and $R_{17}$ is as defined above for formula 10. In a more preferred embodiment, $R_{17}$ is selected from the group consisting of hydrogen, alkyl, aryl, formyl, acyl, alkoxycarbonyl, benzyl and sulfonamide.

For example, specific β,γ-bicyclic ketone compounds corresponding to formula 11A are 1-(2-chloro-4,5-dihydroxybenzyl)-1,2,3,4,7,8-hexahydroisoquinolin-6(5H)-one;
(R)-1-(2-chloro-4,5-dihydroxybenzyl)-1,2,3,4,7,8-hexahydroisoquinolin-6(5H)-one;
(S)-1-(2-chloro-4,5-dihydroxybenzyl)-1,2,3,4,7,8-hexahydroisoquinolin-6(5H)-one;
1-(2-chloro-4,5-dihydroxybenzyl)-3,4,5,6,7,8-hexahydro-6-oxoisoquinoline-2(1H)carbaldehyde;
(R)-1-(2-chloro-4,5-dihydroxybenzyl)-3,4,5,6,7,8-hexahydro-6-oxoisoquinoline-2(1H)carbaldehyde;
(S)-1-(2-chloro-4,5-dihydroxybenzyl)-3,4,5,6,7,8-hexahydro-6-oxoisoquinoline-2(1H)carbaldehyde;
1-(2-bromo-4,5-dihydroxybenzyl)-1,2,3,4,7,8-hexahydroisoquinolin-6(5H)-one;
(R)-1-(2-bromo-4,5-dihydroxybenzyl)-1,2,3,4,7,8-hexahydroisoquinolin-6(5H)-one;
(S)-1-(2-bromo-4,5-dihydroxybenzyl)-1,2,3,4,7,8-hexahydroisoquinolin-6(5H)-one;
1-(2-bromo-4,5-dihydroxybenzyl)-3,4,5,6,7,8-hexahydro-6-oxoisoquinoline-2(1H)carbaldehyde;
(R)-1-(2-bromo-4,5-dihydroxybenzyl)-3,4,5,6,7,8-hexahydro-6-oxoisoquinoline-2(1H)carbaldehyde; and
(S)-1-(2-bromo-4,5-dihydroxybenzyl)-3,4,5,6,7,8-hexahydro-6-oxoisoquinoline-2(1H)carbaldehyde.

Among other factors affecting the yield of the Grewe cyclization reaction is the acidity of the reaction medium. There is an optimum acidity range that advantageously maximizes the rate of the Grewe cyclization reaction and minimizes the rate of the isomerization of the β,γ-hexahydroisoquinolinone starting material into undesirable α,β-hexahydroisoquinolinones. The relative rates of the cyclization and isomerization reactions are affected by the acidity of the reaction medium, which in turn is affected by the properties of the acid catalyst, the conjugate base of the acid catalyst, the solvent, the substrate, impurities and additives to the reaction mixture.

Grewe cyclization utilizes a cyclizing acid that catalyzes the reaction. The cyclizing acid may comprise a strong acid, super acid or combinations thereof. The acid catalyst provides a mixture having sufficient acidity to produce the preferred degree of cyclization. Sufficient acidity of the acid catalyst is primarily determined by the aromatic ring substituents $R_1$, $R_2$, $R_3$, and $R_4$ of the β,γ-bicyclic ketone compound of formula 11. In general, electron donating groups will allow the use of less acidic media for rapid cyclization, one or more neutral or electron withdrawing groups will necessitate the use of super acids. Suitable strong acids are those that are completely ionized in solution, usually water in the case of protic acids. Exemplary strong acids may be selected from the group consisting of benzenesulfonic acid, hydrochloric acid, hydrobromic acid, hydroiodic acid, methanesulfonic acid, nitric acid, phosphoric acid, polyphosphoric acid, sulfuric acid, trichloroacetic acid, trifluoroacetic acid, p-toluenesulfonic acid and combinations thereof. A preferred cyclizing strong acid comprises methanesulfonic acid or sulfuric acid.

Typically, it is preferred to employ a super acid as the cyclizing acid in order to obtain the desired degree and rate of cyclization of the β,γ-bicyclic ketone compound. Super acids include all protic acids that are stronger than 100% sulfuric acid. Suitable super acids include, but are not limited to, anhydrous hydrogen fluoride, fluorosulfonic acid, perchloric acid, perfluoroalkylsulfonic acids (e.g., perfluoro-1-octanesulfonic acid and trifluoromethanesulfonic acid) and combinations thereof or combinations with one or more Lewis acids such as antimony pentafluoride, boron trifluoride, phosphorous pentafluoride and tantalum (V) fluoride. Some combinations of strong acids with super acids may also provide a mixture of sufficient acidity to produce the preferred degree of cyclization, including, for example, sulfuric or polyphosphoric acid combined with trifluoromethanesulfonic acid and/or fluorosulfonic acid. It may also be possible to employ certain inorganic solids of the general formula $M_xO_y$, as a super acid in catalyzing the Grewe reaction, such as sulfated oxides of zirconium(IV), titanium (IV), iron, molybdenum, tungsten, tin(IV), lanthanum and combinations thereof, optionally supported on silica and or alumina substrates. Polymeric bound acids such as perfluorinated ion exchange polymers (e.g., NAFION acidic resin available from DuPont Co.) optionally in combination with other super acids can be used. Preferably, the cyclizing acid is a super acid and comprises trifluoromethanesulfonic acid.

The super acid concentration or strong acid concentration in the Grewe cyclization reaction mixture varies depending on the identity of the acid used. For example, the acid concentration range can be from about two equivalents to about twelve equivalents; preferably, from about six equivalents to about ten equivalents based on the concentration of the β,γ-bicyclic ketone starting material.

The Grewe cyclization of β,γ-bicyclic ketones is suitably carried out in an organic solvent. Typically, the β,γ-bicyclic ketone starting material is combined with the organic solvent prior to contacting the cyclizing acid to form the Grewe reaction mixture. Suitable organic solvents are selected from the group consisting of chloroform, dichloromethane, diethyl ether, tetrahydrofuran, ethyl acetate, methyl sulfone, tetramethylene sulfone and combinations thereof. Preferably, the organic solvent comprises chloroform.

Preferably, the Grewe cyclization is conducted under inert atmosphere (e.g., argon or nitrogen gas) and the reaction mixture cooled and maintained at a reduced temperature during introduction of the cyclizing acid since higher reaction temperatures tend to lead to more side reaction by-products and less of the desired nordihydrothebainone product. Preferably, the temperature of the Grewe reaction mixture is maintained below about 15° C., more preferably, from about −10° C. to about 15° C., and even more preferably from about −5° C. to about 5° C. as the cyclizing acid and the solution of β,γ-bicyclic ketone in a solvent described below are being mixed.

The yield and reproducibility of the Grewe reaction is improved in the process of the present invention by utilizing a selected cyclization additive to affect the properties of the Grewe cyclization reaction mixture. For example, the cyclization additive may reduce the concentration of water in the cyclization reaction mixture as the β,γ-bicyclic ketone is transformed to the nordihydrothebainone product. The reduction or elimination of water effectively increases the acidity of the overall reaction medium. Generally, in one aspect of the present invention, the process comprises forming a reaction mixture comprising a β,γ-bicyclic ketone compound, a cyclizing acid and a cyclization additive. Optimally, cyclization additives are selected so as to react with any water present and form an acid that may be subsequently utilized in catalyzing the Grewe reaction. Suitable cyclization additives generally include acid anhydrides, including gaseous sulfur trioxide and solid phosphorus pentoxide and combinations thereof. Anhydrous molecular sieves compatible with the super acid media may also be used.

In accordance with a preferred embodiment of the present invention, a nordihydrothebainone product is prepared by contacting the β,γ-bicyclic ketone compound with a cyclizing acid in the presence of an acid anhydride as a cyclization additive. The acid anhydrides used may comprise any anhydride of the cyclizing strong and super acids noted above. For example, the acid anhydride can be selected from the group consisting of methanesulfonic anhydride, sulfur trioxide or solutions in sulfuric acid (i.e., fuming sulfuric acid or oleums), phosphorous pentoxide or mixtures of phosphorous pentoxide in phosphoric acid (i.e., polyphosphoric acid), trifluoroacetic anhydride, trifluoromethanesulfonic anhydride, and combinations thereof. When a gaseous anhydride is used (e.g., $SO_3$), fuming sulfuric acid is added to the reaction medium. In accordance with one preferred embodiment, the acid anhydride corresponds to the strong acid or super acid used as the cyclizing acid. Use of the corresponding acid anhydride not only aids in reducing the concentration of water in the Grewe reaction mixture that may lead to undesired side reactions, but the acid anhydride reacts with any water present and produces additional strong or super acid thereby reducing the cyclizing acid demands. In accordance with a preferred embodiment, the cyclizing acid and the acid anhydride are trifluoromethanesulfonic acid and trifluoromethanesulfonic anhydride, respectively.

The cyclization additive such as an acid anhydride is used to reduce the water concentration in the cyclization reaction mixture and inhibit potential yield-reducing side reactions. Water may be introduced into the Grewe reaction mixture from several sources including the cyclizing acid catalyst, the source of the β,γ-bicyclic ketone as well as the organic solvent in which the reaction takes place.

Preferably, the β,γ-bicyclic ketone compound is heated (e.g., at a temperature less than about 60° C.) under vacuum for several days to reduce the concentration of water present. Additionally or alternatively, the β,γ-bicyclic ketone compound may be dissolved in a suitable organic solvent for the Grewe reaction (e.g., chloroform) and to further dry the solution a desiccant such as anhydrous magnesium sulfate may be added. If the suitable organic solvent forms an azeotrope with water then part or all of the solvent with water may be removed by distillation. Further, the chloroform or ether organic solvent is preferably selected to be of a grade that does not include ethanol as a stabilizer since the presence of ethanol, like water, is believed to have an adverse impact on the selectivity of the Grewe reaction.

In one embodiment, the cyclizing acid is combined with an acid anhydride prior to being used in the Grewe cyclization of the β,γ-bicyclic ketone compound in order to reduce the water content present in the cyclizing acid thus reducing the formation of the α,β-ketone by-product and other undesired side reactions. Preferably, the amount of acid anhydride used to treat the cyclizing acid is in slight excess relative to the water concentration such that substantially all of the water present in the acid reacts with the acid anhydride with additional acid anhydride remaining in the treated acid available to react with any water introduced into the Grewe reaction mixture when combined with the β,γ-bicyclic ketone solution.

When an acid anhydride is used as the cyclization additive, it typically has a much lower boiling point than the corresponding cyclizing acid. For example, the boiling point of trifluoromethanesulfonic anhydride is about 81-83° C., while the boiling point of trifluoromethanesulfonic acid is about 167-170° C. Accordingly, in such an embodiment, the acid anhydride is added to the cyclizing acid and the mixture continuously refluxed while monitoring the vapor temperature of the mixture. As the acid anhydride is added to the cyclizing acid, any water present reacts with the anhydride to form the corresponding acid. The acid anhydride is added until a marked decrease in the vapor temperature of the refluxing mixture is observed indicating that the amount of acid anhydride added to the mixture is sufficient to substantially react with any water and excess anhydride is present in the mixture. Typically, the acid anhydride is added until the vapor temperature of the refluxing acid and anhydride mixture decreases to at least about 20° C. below the original vapor temperature of the refluxing acid prior to addition of the acid anhydride. Any acid anhydride distilled from the refluxing mixture during this treatment may be recovered for reuse.

Generally, the amount of excess acid anhydride present in the Grewe cyclization reaction mixture is from about 1 wt. % to about 20 wt. % based on the total weight of the β,γ-bicyclic ketone compound, the cyclizing acid, the acid anhydride and the solvent.

In order to maintain the desired reaction temperature as discussed above during Grewe transformation of the of β,γ-bicyclic ketone compound, the mixture of the cyclizing acid and excess acid anhydride is preferably cooled, typically below about 15° C. (e.g., from about −5° C. to about −10° C.) before being combined with the of β,γ-bicyclic ketone compound diluted in the organic solvent to form the Grewe reaction mixture. Typically, the organic solvent containing the β,γ-bicyclic ketone starting material is added to the cooled mixture of cyclizing acid and remaining acid anhydride at a continuous rate while agitating the resulting Grewe reaction mixture. For example, the solution of the β,γ-bicyclic ketone starting material in the organic solvent may be added to the cyclizing acid and acid anhydride mixture over a period from about 10 to about 60 minutes.

Excess anhydride or other cyclization additive present in the cyclizing acid is available to reduce or eliminate any water present in the β,γ-bicyclic ketone solution when combined to form the Grewe reaction mixture. Acid anhydride or other cyclization additive may be initially or additionally introduced into the Grewe cyclization reaction mixture. It is preferred to have the acid anhydride present when the cyclizing acid and β,γ-bicyclic ketone compound are initially combined. In any event, since the reaction of water and acid anhydride or other cyclization additive can be highly exothermic, proper measures should be employed to cool the Grewe reaction mixture as needed to maintain the desired reaction temperature during the acid-catalyzed transformation of the β,γ-bicyclic ketone compound.

Once addition of the solution of the β,γ-bicyclic ketone compound in organic solvent to the cyclizing acid is complete, agitation of the Grewe reaction mixture is continued and the reaction mixture is typically warmed slightly, for example, to a temperature of from about 10° C. to about 25° C. The acid-catalyzed Grewe transformation is allowed to continue for a time sufficient to transform substantially all of the β,γ-bicyclic ketone compound to the desired nordihydrothebainone product and α,β-bicyclic ketone by-products as determined, for example, by thin-layer chromatography (TLC) or other suitable method. Typically, the duration of the Grewe cyclization reaction after the β,γ-bicyclic ketone compound and cyclizing acid reagents have been combined is from about 6 to about 16 hours.

At the conclusion of the Grewe cyclization reaction, the reaction mixture may be quenched. For example, the Grewe reaction mixture may be quenched by the adding of a cooled (e.g., from about −10° C. to about 10° C.) aqueous solvent to the reaction mixture to ensure that any acid anhydride used as the water scavenger is converted to acid. Preferably, the cooled aqueous solvent has a pH of from about 5 to about 9, more preferably, the cooled aqueous solvent has a pH of about 7.

The nordihydrothebainone product may be readily recovered and isolated from the quenched Grewe reaction mixture using techniques known in the art. For example, nordihydrothebainone product may be extracted from the reaction mixture using the organic solvent (e.g., chloroform) in which the Grewe reaction is conducted. Preferably, the quenched Grewe cyclization reaction is extracted multiple times using an organic solvent to maximize the recovery of the nordihydrothebainone product obtained. The organic layers containing the nordihydrothebainone product, α,β-bicyclic ketone by-product, any unreacted β,γ-bicyclic ketone starting compound and other organic components of the Grewe reaction mixture are combined and treated as described in greater detail below to isolate the nordihydrothebainone product and recover the bicyclic ketone compounds.

Isomerization

As described above, the low reactivity of α,β-bicyclic ketone compounds with cyclizing acids under Grewe cyclization reaction conditions reduces the yield of the desired nordihydrothebainone product. Advantageously, the present invention is also directed to conversion or isomerization of an α,β-bicyclic ketone by-product (usually discarded) to a β,γ-bicyclic ketone starting material that can then be recycled to undergo Grewe cyclization to form the desired nordihydrothebainone product.

Thus, in another embodiment, the process of the present invention is directed to the preparation of a β,γ-bicyclic ketone compound having the formula 20:

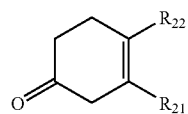

wherein
$R_{21}$ and $R_{22}$ together with the carbons to which they are attached form a 5-, 6- or 7-membered heterocyclic or carbocyclic ring fused to the cyclohexene ring. The process comprises reacting an α,β-bicyclic ketone with a ketone protecting compound to form a protected β,γ-bicyclic ketone compound and hydrolyzing the protected β,γ-bicyclic ketone compound to produce the β,γ-bicyclic ketone compound. Generally, the α,β-bicyclic ketone compound has the structure of formulae 21 or 22 and the protected β,γ-bicyclic ketone compound has the structure of formula 23:

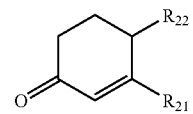

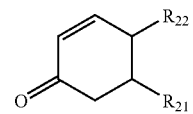

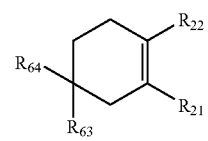

wherein
$R_{21}$ and $R_{22}$ are as defined above, and
$R^{63}$ and $R^{64}$ are independently selected from the group consisting of alkoxy and alkylthio or together with the carbons to which they are attached form a ketal, dithioketal or monothioketal.

The heterocyclic or carbocyclic ring fused to the cyclohexene ring may be selected from the group consisting of pyrrolidyl, piperidyl, tetrahydrofuranyl, tetrahydropyranyl, tetrahydrothiophenyl, cyclopentyl, cyclopentenyl, cyclohexyl, cyclohexenyl, cycloheptyl and cycloheptenyl. In a presently preferred embodiment, the heterocyclic ring fused to the cyclohexene ring is piperidyl.

In one preferred embodiment, the β,γ-bicyclic ketone compound of formula 20 has the structure of formula 25:

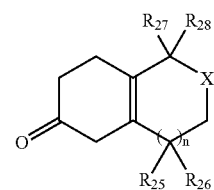

wherein
X is selected from the group consisting of oxygen, sulfur, —S(O)—, —S(O$_2$)—, —C(R$_{18}$R$_{19}$)—, —N(R$_{17}$)— and —N$^+$(R$_{17a}$R$_{17b}$)—;
$R_{25}$, $R_{26}$, $R_{27}$, $R_{28}$, $R_{18}$, and $R_{19}$ are independently selected from the group consisting of hydrogen, acyl, alkenyl, allenyl, alkoxy, alkoxyaryl, alkyl, alkylamino, arylthio, alkylthio, alkynyl, amino, aryl, arylalkoxy, benzyl, substituted benzyl, cyano, carboalkoxy, carbonyl, carboxyalkenyl, carboxyalkyl, carboxyl, cyanoalkyl, cycloalkyl, substituted cycloalkyl, halo, haloalkoxy, haloalkyl, heteroaryl, heterocyclic, hydroxyalkyl, hydroxyl, and nitro;
$R_{17}$ is selected from the group consisting of hydrogen, acyl, alkenyl, alkoxyaryl, alkyl, allyl, alkynyl, aryl, carboxyalkyl, carboxyalkenyl, cyanoalkyl, cycloalkylalkyl, haloalkyl, heteroaryl, heterocyclic, carboxyl, carboxyamide, carboxyester, hydroxyl and hydroxyalkyl;
$R_{17a}$ and $R_{17b}$ are independently selected from the group consisting of hydrogen, alkyl, cycloalkyl, cycloalkylalkyl, aryl and benzyl or together form oxo; and
n is 0, 1 or 2.

When $R_{17}$ is hydrogen, a salt of the secondary amine can form. Exemplary anions for the amine salt are chloride, bromide, acetate, benzoate, formate, sulfate, bisulfate, triflate, fumarate, oxalate, malonate, tartrate, trifluoroacetate or methanesulfonate.

In this preferred embodiment, the α,β-bicyclic ketone compounds of formulae 21 and 22 have the structure of formulae 26 and 27 and the protected β,γ-bicyclic ketone compound of formula 23 has the structure of formula 28:

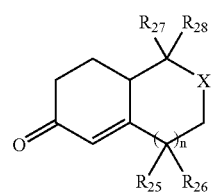

26

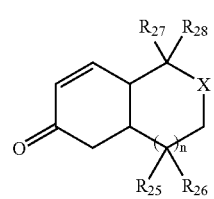

27

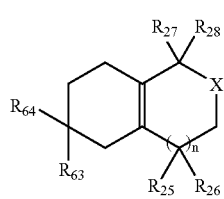

28 wherein n, X, $R_{25}$, $R_{26}$, $R_{27}$, $R_{28}$, $R_{17}$, $R_{18}$, $R_{19}$, $R_{63}$ and $R_{64}$ are as defined above.

In one preferred embodiment, when the starting material and product correspond to formulae 26 or 27 and formula 28, respectively, $R_{25}$ and $R_{26}$ are hydrogen, $R_{27}$ and $R_{28}$ are independently hydrogen or substituted benzyl, X is —N($R_{17}$)—, $R_{63}$ and $R_{64}$ together with the carbon to which they are attached form a 5 or 6-membered ring ketal, and n is 1. In a more preferred embodiment, when the starting material and product correspond to formulae 26 or 27 and formula 28, respectively, $R_{25}$ and $R_{26}$ are hydrogen, $R_{27}$ and $R_{28}$ are independently hydrogen or 2-bromo-5-hydroxy-4-methoxybenzyl, X is —N($R_{17}$)—, $R_{17}$ is —C(O)H, $R_{63}$ and $R_{64}$ together with the carbon to which they are attached form a 5-membered ring ketal, and n is 1.

In a more preferred embodiment, the β,γ-bicyclic ketone compound of formula 20 has the structure of formula 11 described above and the α,β-bicyclic ketone compounds of formulae 21 and 22 have the structure of formulae 30 and 31 and the protected β,γ-bicyclic ketone compound of formula 23 has the structure of formula 32:

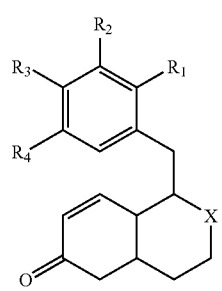

30

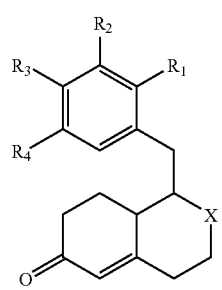

31

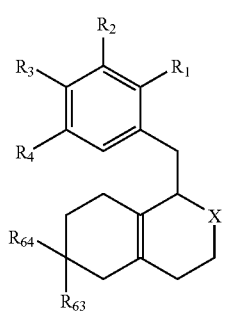

32 wherein

X, $R_1$, $R_2$, $R_3$, $R_4$, $R_{17}$, $R_{18}$ and $R_{19}$ are as defined above for formula 10 and $R_{63}$ and $R_{64}$ are as defined above for formula 23.

In a more preferred embodiment, the α,β-bicyclic ketone compounds of formulae 30 and 31 have the structure of formulae 30A and 31A and the protected β,γ-bicyclic ketone compound of formula 32 has the structure of formula 32A:

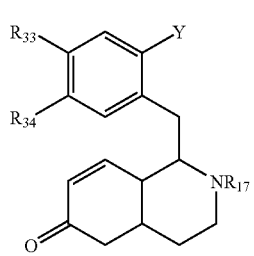

30A

-continued

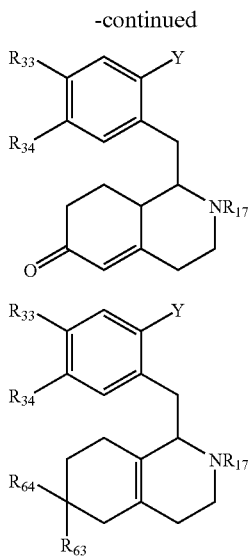

wherein

R$_{33}$ and R$_{34}$ are independently hydroxyl and alkoxy; Y is halo; R$_{17}$ is defined as above for formula 10 and R$_{63}$ and R$_{64}$ are as defined above for formula 23.

Specific α,β-bicyclic ketone compounds useful for this process are
1-(2-chloro-4,5-dihydroxybenzyl)-1,4,4a,5,6,8a-hexahydro-6-oxoisoquinoline-2(3H)-carbaldehyde;
(1R)-1-(2-chloro-4,5-dihydroxybenzyl)-1,4,4a,5,6,8a-hexahydro-6-oxoisoquinoline-2(3H)-carbaldehyde;
(1S)-1-(2-chloro-4,5-dihydroxybenzyl)-1,4,4a,5,6,8a-hexahydro-6-oxoisoquinoline-2(3H)-carbaldehyde;
1-(2-chloro-4,5-dihydroxybenzyl)-1,2,3,4,4a,5-hexahydroisoquinolin-6(8aH)-one;
(1R)-1-(2-chloro-4,5-dihydroxybenzyl)-1,2,3,4,4a,5-hexahydroisoquinolin-6(8aH)-one;
(1S)-1-(2-chloro-4,5-dihydroxybenzyl)-1,2,3,4,4a,5-hexahydroisoquinolin-6(8aH)-one;
1-(2-chloro-4,5-dihydroxybenzyl)-1,2,3,4,8,8a-hexahydroisoquinolin-6(7H)-one;
(1R)-1-(2-chloro-4,5-dihydroxybenzyl)-1,2,3,4,8,8a-hexahydroisoquinolin-6(7H)-one;
(1S)-1-(2-chloro-4,5-dihydroxybenzyl)-1,2,3,4,8,8a-hexahydroisoquinolin-6(7H)-one;
1-(2-bromo-4,5-dihydroxybenzyl)-1,4,4a,5,6,8a-hexahydro-6-oxoisoquinoline-2(3H)-carbaldehyde;
(1R)-1-(2-bromo-4,5-dihydroxybenzyl)-1,4,4a,5,6,8a-hexahydro-6-oxoisoquinoline-2(3H)-carbaldehyde;
(1S)-1-(2-bromo-4,5-dihydroxybenzyl)-1,4,4a,5,6,8a-hexahydro-6-oxoisoquinoline-2(3H)-carbaldehyde;
1-(2-bromo-4,5-dihydroxybenzyl)-1,2,3,4,4a,5-hexahydroisoquinolin-6(8aH)-one;
(1R)-1-(2-bromo-4,5-dihydroxybenzyl)-1,2,3,4,4a,5-hexahydroisoquinolin-6(8aH)-one;
(1S)-1-(2-bromo-4,5-dihydroxybenzyl)-1,2,3,4,4a,5-hexahydroisoquinolin-6(8aH)-one;
1-(2-bromo-4,5-dihydroxybenzyl)-1,2,3,4,8,8a-hexahydroisoquinolin-6(7H)-one;
(1R)-1-(2-bromo-4,5-dihydroxybenzyl)-1,2,3,4,8,8a-hexahydroisoquinolin-6(7H)-one; and
(1S)-1-(2-bromo-4,5-dihydroxybenzyl)-1,2,3,4,8,8a-hexahydroisoquinolin-6(7H)-one.

Specific protected α,β- and β,γ-bicyclic ketone compounds prepared by the processes of the invention are
4-chloro-5-((spiro-6,6-dioxolane-1,2,3,4,6,7,8,8a-octahydroisoquinolin-1-yl)methyl)benzene-1,2-diol;
4-chloro-5-(((1S)-spiro-6,6-dioxolane-1,2,3,4,6,7,8,8a-octahydroisoquinolin-1-yl)methyl)benzene-1,2-diol;
4-chloro-5-(((1R)-spiro-6,6-dioxolane-1,2,3,4,6,7,8,8a-octahydroisoquinolin-1-yl)methyl)benzene-1,2-diol;
1-(2-chloro-4,5-dihydroxybenzyl)-spiro-6,6-dioxolane-3,4,6,7,8,8a-hexahydroisoquinoline-2(1H)-carbaldehyde;
(1S)-1-(2-chloro-4,5-dihydroxybenzyl)-spiro-6,6-dioxolane-3,4,6,7,8,8a-hexahydroisoquinoline-2(1H)-carbaldehyde;
(1R)-1-(2-chloro-4,5-dihydroxybenzyl)-spiro-6,6-dioxolane-3,4,6,7,8,8a-hexahydroisoquinoline-2(1H)-carbaldehyde;
1-(2-chloro-4,5-dihydroxybenzyl)-spiro-6,6-dioxolane-3,4,5,6,7,8-hexahydroisoquinoline-2(1H)-carbaldehyde;
(S)-1-(2-chloro-4,5-dihydroxybenzyl)-spiro-6,6-dioxolane-3,4,5,6,7,8-hexahydroisoquinoline-2(1H)-carbaldehyde;
(R)-1-(2-chloro-4,5-dihydroxybenzyl)-spiro-6,6-dioxolane-3,4,5,6,7,8-hexahydroisoquinoline-2(1H)-carbaldehyde;
4-chloro-5-((spiro-6,6-dioxolane-1,2,3,4,5,6,7,8-octahydroisoquinolin-1-yl)methyl)benzene-1,2-diol;
(S)-4-chloro-5-((spiro-6,6-dioxolane-1,2,3,4,5,6,7,8-octahydroisoquinolin-1-yl)methyl)benzene-1,2-diol;
(R)-4-chloro-5-((spiro-6,6-dioxolane-1,2,3,4,5,6,7,8-octahydroisoquinolin-1-yl)methyl)benzene-1,2-diol;
4-chloro-5-((spiro-6,6-dioxolane-1,2,3,4,4a,5,6,8a-octahydroisoquinolin-1-yl)methyl)benzene-1,2-diol;
4-chloro-5-(((1S)-spiro-6,6-dioxolane-1,2,3,4,4a,5,6,8a-octahydroisoquinolin-1-yl)methyl)benzene-1,2-diol;
4-chloro-5-(((1R)-spiro-6,6-dioxolane-1,2,3,4,4a,5,6,8a-octahydroisoquinolin-1-yl)methyl)benzene-1,2-diol;
1-(2-chloro-4,5-dihydroxybenzyl)-spiro-6,6-dioxolane-1,4,4a,5,6,8a-hexahydroisoquinoline-2(3H)-carbaldehyde;
(1S)-1-(2-chloro-4,5-dihydroxybenzyl)-spiro-6,6-dioxolane-1,4,4a,5,6,8a-hexahydroisoquinoline-2(3H)-carbaldehyde; and
(1R)-1-(2-chloro-4,5-dihydroxybenzyl spiro-6,6-dioxolane-1,4,4a,5,6,8a-hexahydroisoquinoline-2(3H)-carbaldehyde.

Particularly preferred protected α,β-bicyclic ketone compounds formed by the processes of the invention are

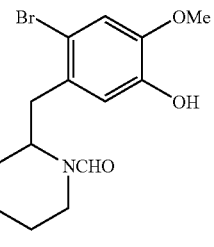

1-(2-bromo-5-hydroxy-4-methoxybenzyl)-spiro-6,6-dioxolane-3,4,6,7,8,8a-hexahydroisoquinoline-2(1H)-carbaldehyde;

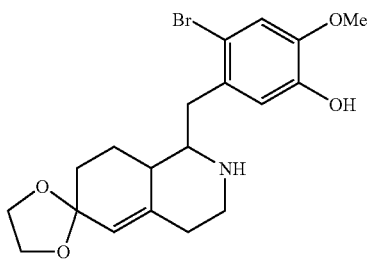

4-bromo-5-((spiro-6,6-dioxolane-1,2,3,4,6,7,8,8a-octahydroisoquinolin-1-yl)methyl)-2-methoxyphenol;

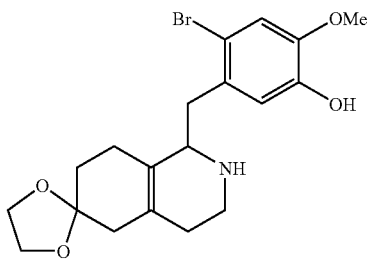

4-bromo-5-((spiro-6,6-dioxolane-1,2,3,4,5,6,7,8-octahydroisoquinolin-1-yl)methyl)-2-methoxyphenol;

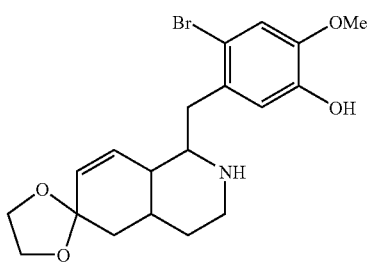

4-bromo-5-((spiro-6,6-dioxolane-1,2,3,4,4a,5,6,8a-octahydroisoquinolin-1-yl)methyl)-2-methoxyphenol; and

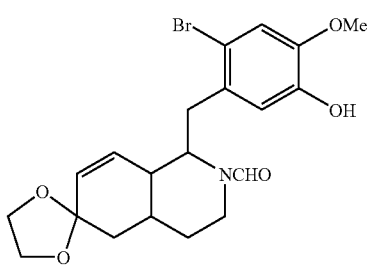

1-(2-bromo-5-hydroxy-4-methoxybenzyl)-spiro-6,6-dioxolane-1,4,4a,5,6,8a-hexahydroisoquinoline-2(3H)-carbaldehyde.

1. Protecting an α,β-Bicyclic Ketone Compound

Generally, to form a protected β,γ-bicyclic ketone compound, an α,β-bicyclic ketone compound is reacted with a protecting compound in an organic medium. Typically, this protecting reaction is carried out in the presence of a protecting acid catalyst. A protecting compound comprises a diol or a dithiol that reacts with a ketone to form a ketal comprising $R_{63}$, $R_{64}$ and the carbon to which they are attached. In one preferred embodiment, the ketone protecting compound is a diol. For example, the ketone protecting compound may be selected from the group consisting of 1,2-ethanediol, 1,2-ethanedithiol, 1,2-propanediol, 1,3-propanediol, 1,2-propanedithiol, 1,3-propanedithiol, 1,2-butanediol, 1,3-butanediol, 2,3-butanediol, 1,2-pentanediol, 2,4-pentanediol, 2,4-dimethyl-2,4-pentanediol, 1,2-hexanediol, 2-ethyl-1,3-hexanediol, 1,2-octanediol, 1,2-decanediol, 1,2-dodecanediol, cis-1,2-cyclopentanediol, trans-1,2-cyclopentanediol, cis-1,2-cyclooctanediol, trans-1,2-cyclooctanediol, (+)-pinanediol, (−)-pinanediol and catechol; enantiomers and combinations thereof.

Protection of the α,β-bicyclic ketone compound is carried out in an organic medium. Preferably, the organic solvent is selected from the group consisting of chloroform, dichloromethane, toluene, chlorobenzene, xylene, diethyl ether, ethyl acetate, the ketone protecting compound, and combinations thereof. More preferably, the organic medium comprises the ketone protecting compound.

The protecting acid catalyst may be selected from the group consisting of but not limited to methanesulfonic acid, p-toluenesulfonic acid, sulfuric acid, phosphoric acid, trifluoroacetic acid, trichloroacetic acid, oxalic acid, boron trifluoride, and combinations thereof. In some cases, lithium or magnesium salts may be used such as magnesium triflate or lithium hexafluorophosphate.

The reaction temperature for the step of protecting the α,β-bicyclic ketone compound is typically from about 0° C. to about 50° C., preferably from about 10° C. to about 30° C., for example about 20° C.

The duration of the α,β-bicyclic ketone protecting step is generally from about 30 minutes to about 3 hours, preferably, about 1 hour.

In one embodiment, the reaction forming the protected β,γ-bicyclic ketone product, represented by formulae 23 or 28, is quenched by addition of an alkaline aqueous solution to neutralize the protecting acid catalyst. The alkaline aqueous solution is selected from the group consisting of ammonium carbonate, ammonium bicarbonate, sodium carbonate, sodium bicarbonate, potassium carbonate, potassium bicarbonate, ammonium hydroxide, potassium hydroxide, sodium hydroxide, sodium phosphate, potassium phosphate, sodium hydrogenphosphate and potassium hydrogenphosphate, and combinations thereof.

The protected β,γ-bicyclic ketone product may be isolated from the reaction mixture by extraction. For example, the quenched reaction mixture containing the protected β,γ-bicyclic ketone product can be extracted using an organic solvent. Preferably, the organic solvent is selected from the group consisting of chloroform, dichloromethane, 1,2-dichloroethane, chlorobenzene, diethyl ether, ethyl acetate, and combinations thereof. More preferably, the organic solvent comprises chloroform. Extraction of the quenched reaction mixture can be carried out multiple times to maximize recovery of the protected β,γ-bicyclic ketone product.

Further, the combined extracted organic layers can be washed. For example, the combined extracted organic layers can be washed with an aqueous solution. Preferably, the aqueous solution is water. The organic layer can be washed multiple times to maximize the removal of compounds soluble in water (e.g., neutralized protecting acid, quenching aqueous base, and the like).

Finally, the combined, washed organic layers can be dried by treatment with an anhydrous salt, molecular sieves or azeotropic removal of water. After dehydration, any volatiles can be removed from the combined organic layers by distillation followed by vacuum drying.

In an alternative embodiment, the protected β,γ-bicyclic ketone compound is not dried prior to hydrolyzing it with a deprotecting acid to form the unprotected β,γ-bicyclic ketone compound as described below.

2. Hydrolysis of the Protected β,γ-Bicyclic Ketone Compound

To produce the β,γ-bicyclic ketone compound, the protected β,γ-bicyclic ketone compound having the structure of formulae 23 or 28 is carefully hydrolyzed using a deprotecting acid to form the corresponding unprotected β,γ-bicyclic ketone compound having the structure of formulae 20 or 25.

In one preferred embodiment, when the protected β,γ-bicyclic ketone compound corresponds to formula 28 and the unprotected β,γ-bicyclic ketone compound corresponds to formula 25, $R_{25}$ and $R_{26}$ are hydrogen, $R_{27}$ and $R_{28}$ are independently hydrogen and substituted benzyl, X is —N($R_{17}$)—, $R_{63}$ and $R_{64}$ together with the carbon to which they are attached comprise a 5 or 6-membered ring ketal, and n is 1. In a more preferred embodiment, for the protected and unprotected β,γ-bicyclic ketone compounds, $R_{25}$ and $R_{26}$ are hydrogen, $R_{27}$ and $R_{28}$ are independently hydrogen and 2-bromo-5-hydroxy-4-methoxybenzyl, X is —N($R_{17}$)—, $R_{17}$ is formyl (i.e., —C(O)H), $R_{63}$ and $R_{64}$ together with the carbon to which they are attached form a 5-membered ring (ethylene) ketal, and n is 1.

Hydrolysis of the protected β,γ-bicyclic ketones is carried out by reacting the protected β,γ-bicyclic ketones in an aqueous acidic deprotecting medium. Numerous deprotecting acids can be used to carry out the hydrolysis of protected β,γ-bicyclic ketones. Preferably, the deprotecting acid is selected from the group consisting of acetic acid, oxalic acid, formic acid, hydrochloric acid, sulfuric acid, methanesulfonic acid, hydrobromic acid, trifluoroacetic acid and combinations thereof. In a presently preferred embodiment, the deprotecting acid comprises formic acid. Preferably, the hydrolysis of protected β,γ-bicyclic ketones is carried out at a pH of below at least about 7. More preferably, the hydrolysis of protected β,γ-bicyclic ketone compound is carried out at a pH of from about 3 to about 6.

The temperature of the hydrolysis reaction is suitably from about 0° C. to about 50° C. Preferably, the temperature of the hydrolysis reaction is from about 10° C. to about 30° C. and more preferably is about 20° C.

The protected β,γ-bicyclic ketone compound is generally contacted with the deprotecting acid for about 30 minutes to about 3 hours, preferably, for about 1 hour.

In one embodiment, the β,γ-bicyclic ketone product of the hydrolysis reaction is obtained by extraction techniques known in the art. For example, the hydrolysis reaction mixture is diluted with water and then the β,γ-bicyclic ketone product is extracted from the hydrolysis reaction mixture using an organic solvent. Preferably, the organic solvent is selected from the group consisting of chloroform, toluene, chlorobenzene, 1,2-dichloroethane, dichloromethane, diethyl ether, ethyl acetate, and combinations thereof. More preferably, the organic solvent comprises chloroform. The extraction of β,γ-bicyclic ketone product can be carried out multiple times to maximize the recovery of the β,γ-bicyclic ketone product.

Further, the combined organic layers can be washed to remove water soluble components. For example, a method of washing the combined organic layers comprises washing the combined organic layers with an acidic aqueous solution. Preferably, the acidic aqueous solution is selected from the group consisting of acetic acid, formic acid, hydrochloric acid, sulfuric acid, phosphoric acid, hydrobromic acid, methanesulfonic acid, and combinations thereof. More preferably, the aqueous solution comprises formic acid. Optionally, an acidic buffered solution may be used. To maximize the removal of compounds soluble in water, the process of washing the combined organic layers can be carried out multiple times.

The combined washed organic layers can be dried by techniques known in the art. For example, the combined washed organic layers are dried under vacuum after removal of any volatile solvents, usually by distillation.

Integration of Grewe Cyclization and Isomerization

Another aspect of the invention is directed to integrating the Grewe cyclization of a β,γ-bicyclic ketone with conversion of α,β-bicyclic ketone by-products to starting β,γ-bicyclic ketone compounds for recycle and transformation in the Grewe step.

Grewe cyclization of β,γ-bicyclic ketones typically results in undesired α,β-bicyclic ketone by-product formation as disclosed above and by Rice in U.S. Pat. No. 4,368,326. Previously this α,β-bicyclic ketone by-product was typically separated and discarded from the desired nordihydrothebainone product. In one embodiment of the process of the present invention, the α,β-bicyclic ketone by-products can be converted to the corresponding starting β,γ-bicyclic ketone compound and recycled to the Grewe cyclization step. By integrating the α,β- to β,γ-interconversion of bicyclic ketones with the Grewe cyclization reaction, the overall yield for the synthesis of nordihydrothebainone and analogs thereof may be improved.

In a preferred embodiment of the present invention, the improved Grewe cyclization step incorporating a cyclization additive is integrated with the conversion of α,β- to β,γ-bicyclic ketone compounds. In a presently preferred embodiment, the Grewe cyclization reaction takes place in the presence of an acid anhydride. The reaction conditions for the Grewe cyclization are as described above. The combination of using the improved Grewe cyclization step with a higher reaction yield and a process of converting the α,β- to β,γ-bicyclic ketone and recycling it to the Grewe step maximizes the overall yield of the nordihydrothebainone product.

For example, the process of the present invention is directed to the preparation of nordihydrothebainone or an analog thereof having the formula 10 wherein the process comprises acid catalyzed cyclization of a β,γ-bicyclic ketone compound having the structure of formula 11 to form the nordihydrothebainone product and an α,β-bicyclic ketone by-product (formulae 30 or 31) in a Grewe reaction zone. In an isomerization reaction zone, the α,β-bicyclic ketone by-product of the Grewe transformation, is reacted with a ketone protecting compound to form a protected β,γ-bicyclic ketone compound (formula 32) and the protected β,γ-bicyclic ketone compound hydrolyzed to form the β,γ-bicyclic ketone compound of formula 11. Preferred embodiments of compounds corresponding to formulae 10, 11, 30, 31 and 32 are described above.

As described above, the cyclization reaction medium can be quenched and extracted with an organic solvent, thus producing extracted organic layers containing the nordihydrothebainone product, the α,β-bicyclic ketone by-products and unreacted β,γ-bicyclic ketone starting material. The combined organic layers from the Grewe cyclization step are washed with a basic aqueous solution. The result of washing the organic layer is that the nordihydrothebainone product remains in the organic layer, while α,β-bicyclic ketone by-products, represented by formulae 21, 22, 26, 27, 30, 30A, 31 and 31A and unreacted β,γ-bicyclic ketone starting material represented by formulae 11, 20 and 25 are transferred to the basic aqueous solution.

Although the specific conditions for isolating the desired nordihydrothebainone product may be specific to the particular substitution pattern of the β,γ-bicyclic ketone starting material and the product, a person of ordinary skill would know how to modify the general procedure detailed here. Generally, the pH of the basic aqueous solution is adjusted to about 11 to about 13. The basic aqueous solution can be selected from the group consisting of potassium hydroxide, sodium hydroxide, sodium phosphate, and combinations thereof. More preferably, the basic aqueous solution comprises sodium phosphate. Preferably, the organic layer is washed multiple times with the basic aqueous solution to maximize the separation of the desired nordihydrothebainone product from the α,β-bicyclic ketone by-product and the unreacted β,γ-bicyclic ketone starting material.

The organic layer that has been washed with a basic aqueous solution can be neutralized by washing with an acidic aqueous solution. The acidic aqueous solution can be selected from the group consisting of acetic acid, formic acid, hydrochloric acid, sulfuric acid, hydrobromic acid, phosphoric acid, and combinations thereof. More preferably, the acidic aqueous solution comprises formic acid. Preferably, the organic layer is washed multiple times with the acidic aqueous solution.

Further, the organic layer after washing (e.g., with a basic aqueous solution, an acidic aqueous solution, or both) can be filtered to remove extraneous solid material. For example, the combined organic layers are filtered through a powder. Preferably, the filter powder is selected from the group consisting of potassium carbonate, potassium sulfate, celite, sand, alumina, and combinations thereof. More preferably, the filter powder comprises potassium sulfate.

The washed and filtered organic layer can then be dried by techniques known in the art to obtain solid nordihydrothebainone product. For example, the volatile components of the washed and filtered organic layer may be removed by distillation or distillation under reduced pressure and the remaining solid dried under vacuum.

α,β-Bicyclic ketone by-products and unreacted β,γ-bicyclic ketone starting material can be recovered from the combined basic aqueous solution layers by first acidifying the basic aqueous solution and adding an organic solvent.

After the basic aqueous solution has been acidified, the α,β-bicyclic ketone by-product and unreacted β,γ-bicyclic ketone starting material will be present in the organic layer and separated. Any volatile components of the organic layer are removed by distillation and the remaining solid optionally dried under vacuum. Preferably, the acidifying acid is selected from the group consisting of acetic acid, formic acid, hydrochloric acid, sulfuric acid, phosphoric acid, and combinations thereof. In general, the pH of the solution is from about 1 to 5. The organic solvent used for extraction is selected from the group consisting of chloroform, 1,2-dichloroethane, chlorobenzene, toluene, dichloromethane, diethyl ether, ethyl acetate, and combinations thereof. More preferably, the organic solvent comprises chloroform. Extraction of the combined acidified basic aqueous layers using an organic solvent can be carried out multiple times to maximize the recovery of the α,β-bicyclic ketone by-products and unreacted β,γ-bicyclic ketone starting material.

A solution containing the isolated and recovered α,β-bicyclic ketone by-products and unreacted β,γ-bicyclic ketone starting material in an organic solvent can be reacted with a ketone protecting compound in the presence of a protecting acid catalyst as described above. Once protection and hydrolysis reactions have been performed, the resulting product solution can be worked up as described above. The organic solution of β,γ-bicyclic ketone starting material resulting from the workup of the hydrolysis reaction mixture can be recycled to the Grewe reaction zone to produce additional nordihydrothebainone product.

Definitions

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless the term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics such as furyl, pyridyl, oxazolyl, pyrrolyl, indolyl, quinolinyl, or isoquinolinyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

EXAMPLES

The following examples are simply intended to further illustrate and explain the present invention. The invention, therefore, should not be limited to any of the details in these examples.

Example 1

Conversion of α,β-hexahydroisoquinolinones to protected β,γ-hexahydroisoquinolinone

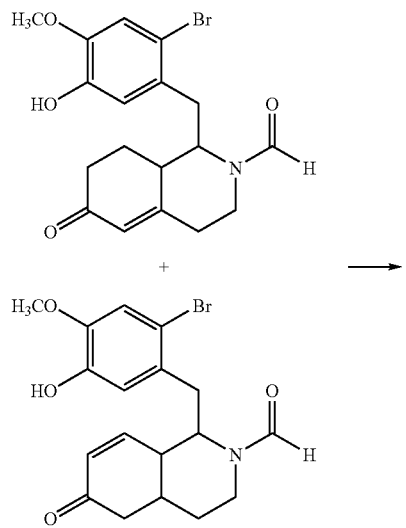

-continued

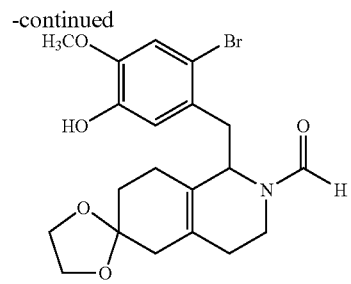

A solution of the isomers 1-(2'-bromo-4'-methoxy-5'-hydroxybenzyl)-2-formyl-1,3,4,7,8-hexahydroisoquinolin-6-one and 1-(2'-bromo-4'-methoxy-5'-hydroxybenzyl)-2-formyl-1,3,4,5-hexahydroisoquinolin-6-one in chloroform solvent was added to ethylene glycol (e.g., ketone protecting compound) over 1 hour to form a solution of 1-(2'-bromo-4'-methoxy-5'-hydroxybenzyl)-2-formyl-6-ketal-1,3,4,5,7,8-hexahydroisoquinoline (>90% area/area by HPLC analysis). The solution was added to 5% $NH_4OH$ (200 mL) to form a suspension that was extracted with chloroform (3×40 mL). The combined organic layers were washed with water (3×100 mL) and placed under vacuum until dry to give the product as a white solid (1.03 g, 80% area/area and 70% w/w/ by HPLC assay).

Example 2

Hydrolysis of protected β,γ-hexahydroisoquinolinone to Unprotected β,γ-hexahydroisoquinolinone

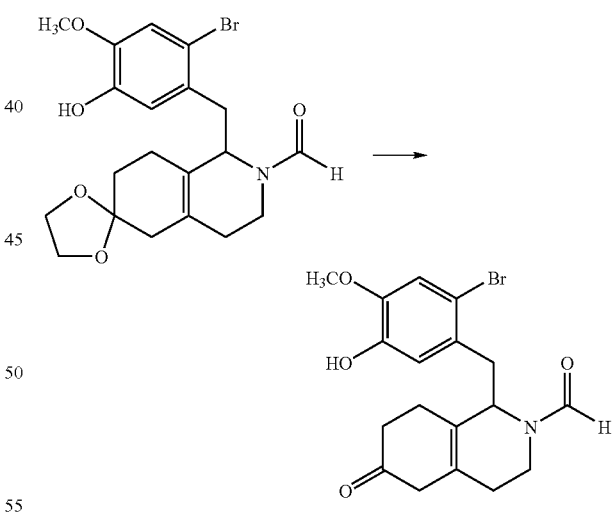

A sample of 1-(2'-bromo-4'-methoxy-5'-hydroxybenzyl)-2-formyl-6-ketal-1,3,4,5,7,8-hexahydroisoquinoline (0.97 g) was dissolved in 10 mL of 88% acetic acid. The resultant solution was stirred for 1 hour at room temperature. After the solution had been stirred for 1 hour, the solution was diluted with 50 mL of $H_2O$ and 40 mL of chloroform, swirled, and then poured into a 500 mL separatory funnel. The mixture was mixed and vented and the organic layer was separated. Another 40 mL of chloroform was added to the aqueous layer. The solution was repeatedly mixed and vented and the organic layer was once again separated leaving the aqueous layer in the separatory funnel. Once again 40 mL of chloroform was added to the aqueous layer. The solution was swirled again and the organic layer was once again separated leaving the aqueous layer in the separatory funnel. The organic layer was washed with 100 mL of 1% formic acid once again using a 500 mL separatory funnel. The organic layer was separated and then another 100 mL of 1% formic acid was added to organic layer and this solution was placed in a 500 mL separatory funnel. The solution was mixed and vented and then the organic layer was separated. The organic layer was then added to 100 mL of $H_2O$ and placed in a 500 mL separatory tunnel. The organic layer was then separated and placed into a 250 mL flask and placed under vacuum. The resulting product was a yellow solid weighing 0.77 g and consisted of 94% area/area 1-(2'-bromo-4'-methoxy-5'-hydroxybenzyl)-2-formyl-1,3,4,5,7,8-hexahydroisoquinolin-6-one (e.g., β,γ-hexahydroisoquinolinone) as determined by HPLC assay.

Example 3

Grewe Cyclization Step

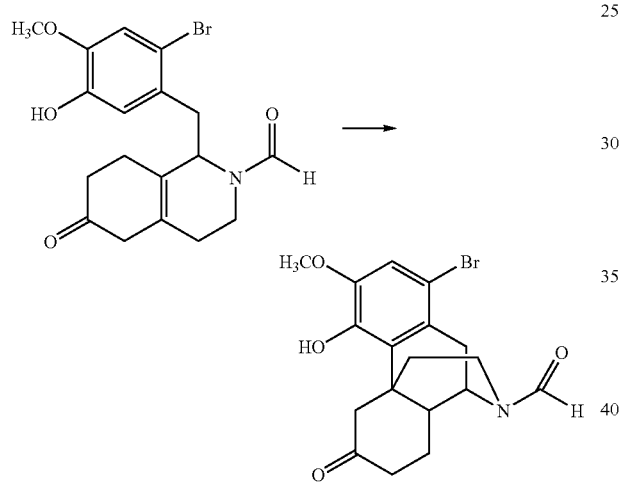

A mixture of 270 mL of 98% trifluoromethane sulfonic acid and 60 mL 99% trifluoromethanesulfonic anhydride was added to a 2 L round bottom flask. The mixture was heated to reflux and the vapor temperature reached to between 88° C. to 130° C. The solution was cooled to between 5° C. to 10° C. under $N_2$. A solution of 100 g 1-(2'-bromo-4'-methoxy-5'-hydroxybenzyl)-2-formyl-1,3,4,5,7,8-hexahydroisoquinolin-6-one (e.g., β,γ-hexahydroisoquinolinone) dissolved in 750 mL of $CHCl_3$ was placed in a 1 L round bottom flask and was put under nitrogen. The β,γ-hexahydroisoquinolinone solution was added to the trifluoromethanesulfonic acid solution at a constant rate over a period of 30 minutes and constantly stirred. The trifluoromethanesulfonic acid solution was surrounded by an ice bath in order to keep the temperature of the solution under 15° C. during the addition of the β,γ-hexahydroisoquinolinone. After the combination of the solutions was complete, the reaction was allowed to warm up to room temperature and stirred for about 12 hours. Following the stirring at room temperature, the reaction mixture was added to a mixture of 600 mL of $H_2O$ and 300 g of ice and stirred. The mixture was then placed in a 2 L separatory funnel and mixed and vented. The organic layer containing the product was separated and retained. The aqueous layer was extracted with 100 mL chloroform after mixing and venting using a separatory funnel. The organic layers were combined and washed with 600 mL of 3% $Na_3PO_4$. The pH of each wash was adjusted to 12 using 1 N NaOH. The organic layer was then separated and washed 3 more times using the aforementioned $Na_3PO_4$ wash procedure to remove the unreacted β,γ-hexahydroisoquinolinone and α,β-hexahydroisoquinolinone by-product. The resulting organic layer containing the nordihydrothebainone product was then washed with 600 mL 3% $HCO_2H$ by adding both solutions to a 2 L separatory funnel and then mixing and venting. The organic layer was then separated and filtered through a bed of 50 g of $K_2SO_4$ powder. The $K_2SO_4$ powder was then washed with 25 mL of $CHCl_3$ twice. The organic layers were combined and dried under vacuum and kept at 60° C. for 3 hours to yield 96 g of solid. The product was 95% area/area 1-bromo-N-formylnordihydrothebainone as determined by HPLC analysis.

The present invention is not limited to the above embodiments and can be variously modified. The above description of preferred embodiments is intended only to acquaint others skilled in the art with the invention, its principles and its practical application so that others skilled in the art may adapt and apply the invention in its numerous forms, as may be best suited to the requirements of a particular use.

With reference to the use of the word(s) "comprise" or "comprises" or "comprising" in this entire specification (including the claims below), it is noted that unless the context requires otherwise, those words are used on the basis and clear understanding that they are to be interpreted inclusively, rather than exclusively, and that it is intended each of those words to be so interpreted in construing this entire specification.

What is claimed is:

1. A process for the preparation of a nordihydrothebainone product comprising nordihydrothebainone or an analog thereof having the structure of formula 10:

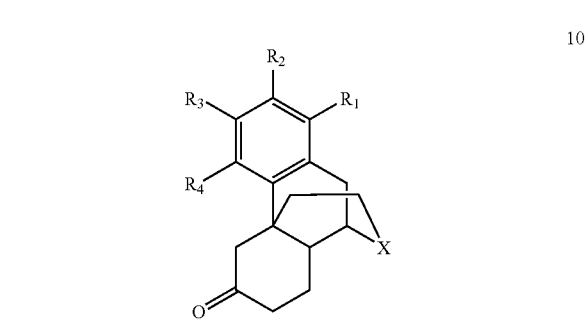

wherein

X is selected from the group consisting of oxygen, sulfur, —S(O)—, —S(O_2)—, —C(R_{18}R_{19})—, —N(R_{17})— and —N^+(R_{17a}R_{17b})—;

$R_1$, $R_2$, $R_3$, $R_4$, $R_{18}$, and $R_{19}$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro, or $R_{18}$ and $R_{19}$ together form keto;

$R_{17}$ is selected from the group consisting of hydrogen, acyl, alkenyl, alkoxyaryl, alkyl, alkynyl, aryl, carboxyalkenyl, carboxyalkyl, cyanoalkyl, cycloalkyl, cycloalkylalkyl, haloalkyl, heteroaryl, heterocyclic, carboxyl, carboxyamide, carboxyester, hydroxyl and hydroxyalkyl; and R$_{17a}$ and R$_{17b}$ are independently selected from the group consisting of hydrogen, alkyl, cycloalkyl, cycloalkylalkyl, aryl and benzyl or together form oxo;

the process comprising:

forming a reaction mixture comprising a β,γ-bicyclic ketone compound, a cyclizing acid and an acid anhydride to produce the nordihydrothebainone product, the β,γ-bicyclic ketone compound having the structure of formula 11:

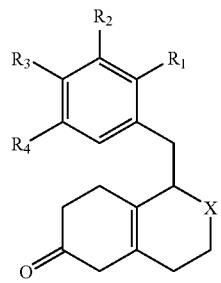

11 wherein

X, R$_1$, R$_2$, R$_3$, R$_4$, R$_{17}$, R$_{18}$ and R$_{19}$ and are as defined above.

2. The process as set forth in claim 1 wherein the cyclizing acid comprises a super acid selected from the group consisting of anhydrous hydrogen fluoride, fluorosulfonic acid, perchloric acid, perfluoroalkylsulfonic acids, perfluoroethanesulfonic acid, trifluoromethanesulfonic acid and combinations thereof or combinations with one or more Lewis acids.

3. The process as set forth in claim 1 wherein the acid anhydride comprises an anhydride of a strong acid or a super acid and the acid anhydride corresponds to the strong acid or super acid used as the cyclizing acid.

4. The process as set forth in claim 1 wherein the acid anhydride and the super acid are trifluoromethanesulfonic anhydride and trifluoromethanesulfonic acid respectively.

5. The process as set forth in claim 1 wherein X is —N(R$_{17}$)—.

6. The process as set forth in claim 1 wherein the β,γ-bicyclic ketone compound is 1-(2'-bromo-4'-methoxy-5'-hydroxybenzyl)-2-formyl-6-oxo-1,3,4,5,7,8-hexahydroisoquinoline, the cyclizing acid is a super acid, the acid anhydride corresponds to the super acid and the nordihydrothebainone product comprises 1-bromo-N-formylnordihydrothebainone.

7. The process as set forth in claim 1 further comprising converting the nordihydrothebainone product of formula 10 to a compound of formula 1 having the structure:

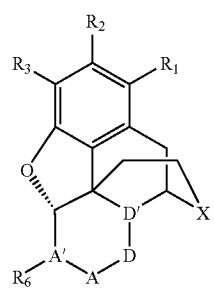

1 wherein

-A'-A- represents the group

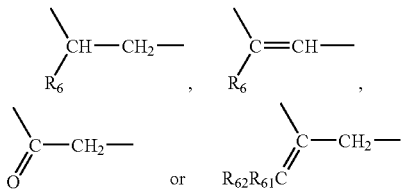

-D-D'- represents the group

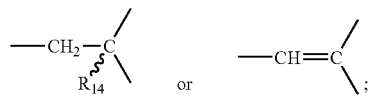

-A-D- represents the group —CH$_2$CH$_2$— or —CH=CH— or =CH—CH=;

X is selected from the group consisting of oxygen, sulfur, —S(O)—, —S(O$_2$)—, —N(R$_{17}$)— and —N$^+$(R$_{17a}$R$_{17b}$—;

R$_1$ and R$_2$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro;

R$_3$ is selected from the group consisting of alkoxy, hydroxyl and acetoxy;

R$_6$ is selected from the group consisting of alkoxy, hydroxyl and acetoxy;

R$_{14}$ is selected from the group consisting of hydrogen, hydroxyl and acetoxy;

R$_{17}$ is selected from the group consisting of lower alkyl, alkylenecycloalkyl, allyl alkenyl, acyl, formyl, formyl ester, formamide and benzyl;

R$_{17a}$ and R$_{17b}$ are independently selected from the group consisting of hydrogen, alkyl, cycloalkyl, cycloalkylalkyl, aryl and benzyl;

R$_{18}$, and R$_{19}$ are independently selected from the group consisting of hydrogen, substituted and unsubstituted acyl, alkenyl, alkoxy, alkoxyaryl, alkyl, alkylamino, arylthio, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, halo, haloalkoxy, haloalkyl, heteroaryl, heterocyclic, hydroxyalkyl, hydroxyl and nitro or R$_{18}$ and R$_{19}$ together form keto; and R$_{61}$ and R$_{62}$ are independently selected from hydrogen, alkyl, alkenyl, alkynyl and aryl;

provided that if -A-D- is —CH=CH—, then -A'-A- is other than —C(R$_6$)=CH— and -D-D'- is other than

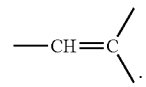

8. A process for the preparation of a nordihydrothebainone product comprising nordihydrothebainone or an analog thereof having structure of formula 10:

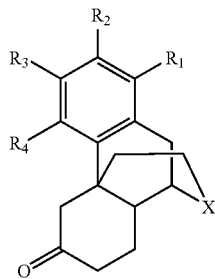

10 wherein
X is selected from the group consisting of oxygen, sulfur, —S(O)—, —S(O$_2$)—, —C(R$_{18}$R$_{19}$)—, —N(R$_{17}$)— and —N$^+$(R$_{17a}$R$_{17b}$)—;
R$_1$, R$_2$, R$_3$, R$_4$, R$_{18}$, and R$_{19}$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro, or R$_{18}$ and R$_{19}$ together form keto;
R$_{17}$ is selected from the group consisting of hydrogen, acyl, alkenyl, alkoxyaryl, alkyl, alkynyl, aryl, carboxyalkenyl, carboxyalkyl, cyanoalkyl, cycloalkyl, cycloalkylalkyl, haloalkyl, heteroaryl, heterocyclic, carboxyl, carboxyamide, carboxyester, hydroxyl and hydroxyalkyl; and
R$_{17a}$ and R$_{17b}$ are independently selected from the group consisting of hydrogen, alkyl, cycloalkyl, cycloalkylalkyl, aryl and benzyl or together form oxo;
the process comprising:
forming a reaction mixture comprising a β,γ-bicyclic ketone compound and a cyclizing acid in a Grewe reaction zone to produce a Grewe product mixture comprising the nordihydrothebainone product and an α,β-bicyclic ketone compound by-product, the β,γ-bicyclic ketone compound having the structure of formula 11:

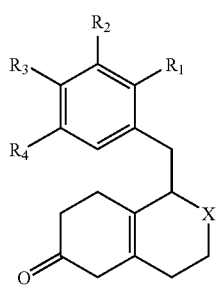

11 wherein
X, R$_1$, R$_2$, R$_3$, R$_4$, R$_{17}$, R$_{18}$ and R$_{19}$ and are as defined above;
reacting the α,β-bicyclic ketone compound by-product obtained in the Grewe product mixture with a ketone protecting compound in an isomerization reaction zone to form a protected β,γ-bicyclic ketone compound, the α,β-bicyclic ketone compound by-product having the structure of formulae 30 or 31 and the protected β,γ-bicyclic ketone compound having the structure of formula 32:

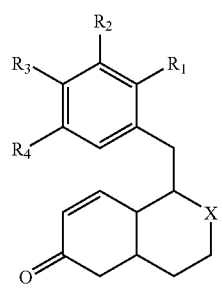

30

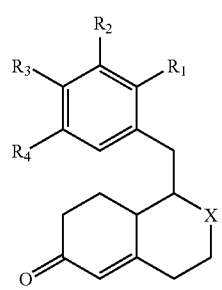

31

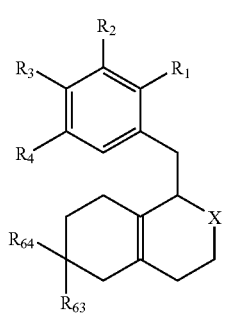

32 wherein
R$_{63}$ and R$_{64}$ are independently selected from the group consisting of alkoxy and alkylthio or together with the carbons to which they are attached form a ketal, dithioketal or monothioketal; and
X, R$_1$, R$_2$, R$_3$, R$_4$, R$_{17}$, R$_{18}$ and R$_{19}$ are as defined above; and
hydrolyzing the protected β,γ-bicyclic ketone compound to form the β,γ-bicyclic ketone compound of formula 11.

9. The process as set forth in claim 8 further comprising introducing the β,γ-bicyclic ketone compound formed by hydrolyzing the protected β,γ-bicyclic ketone compound into the Grewe reaction zone.

10. The process as set forth in claim 8 wherein the ketone protecting compound is selected from the group consisting of 1,2-ethanediol, 1,2-ethanedithiol, 1,2-propanediol, 1,3-propanediol, 1,2-propanedithiol, 1,3-propanedithiol, 2-mercaptoethanol, 1,2-butanediol, 1,3-butanediol, 2,3-butanediol, 1,2-pentanediol, 2,4-pentanediol, 2,4-dimethyl-2,4-pentanediol, 1,2-hexanediol, 2-ethyl-1,3-hexanediol, 1,2-octanediol, 1,2-decanediol, 1,2-dodecanediol, cis-1,2-cyclopentanediol, trans-1,2-cyclopentanediol, cis-1,2-cyclooctanediol, trans-1,2-cyclooctanediol, (+)-pinanediol, (−)-pinanediol, catechol, and enantiomers and combinations thereof.

11. The process as set forth in claim 8 wherein the cyclization reaction of β,γ-bicyclic ketone compound to the nordihydrothebainone product is carried out in the presence of a cyclizing acid and an acid anhydride.

12. The process as set forth in claim 8 wherein the cyclizing acid is selected from the group consisting of strong acids, super acids and combinations thereof and the acid anhydride corresponds to the strong acid or super acid used as the cyclizing acid.

13. The process as set forth in claim 8 wherein the α,β-bicyclic ketone compound is selected from 1-(2'-bromo-4'-methoxy-5'-hydroxybenzyl)-2-formyl-1,3,4,7,8-hexahydroisoquinolin-6-one and 1-(2'-bromo-4'-methoxy-5'-hydroxybenzyl)-2-formyl-1,3,4,5-hexahydroisoquinolin-6-one and the nordihydrothebainone product comprises 1-bromo-N-formylnordihydrothebainone or analogs thereof.

14. The process as set forth in claim 8 further comprising converting the nordihydrothebainone product of formula 10 to a compound of formula 1 having the structure:

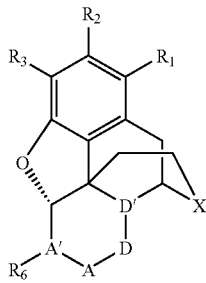

1 wherein

-A'-A- represents the group

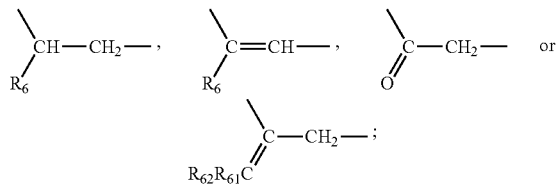

-D-D'- represents the group

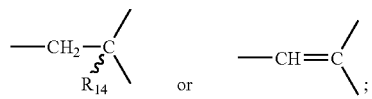

-A-D- represents the group —$CH_2CH_2$— or —CH=CH— or =CH—CH=;

X is selected from the group consisting of oxygen, sulfur, —S(O)—, —S($O_2$)—, —C($R_{18}R_{19}$)—, —N($R_{17}$)— and —$N^+(R_{17a}R_{17b})$—;

$R_1$ and $R_2$ are independently selected from the group consisting of hydrogen, substituted and unsubstituted acyl, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, and nitro;

$R_3$ is selected from the group consisting of alkoxy, hydroxyl and acetoxy;

$R_6$ is selected from the group consisting of alkoxy, hydroxyl and acetoxy;

$R_{14}$ is selected from the group consisting of hydrogen, hydroxyl and acetoxy;

$R_{17}$ is selected from the group consisting of lower alkyl, alkylenecycloalkyl, allyl alkenyl, acyl, formyl, formyl ester, formamide and benzyl;

$R_{17a}$ and $R_{17b}$ are independently selected from the group consisting of hydrogen, alkyl, cycloalkyl, cycloalkylalkyl, aryl and benzyl;

$R_{18}$, and $R_{19}$ are independently selected from the group consisting of hydrogen, substituted and unsubstituted acyl, alkenyl, alkoxy, alkoxyaryl, alkyl, alkylamino, arylthio, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, halo, haloalkoxy, haloalkyl, heteroaryl, heterocyclic, hydroxyalkyl, hydroxyl and nitro or $R_{18}$ and $R_{19}$ together form keto; and $R_{61}$ and $R_{62}$ are independently selected from hydrogen, alkyl, alkenyl, alkynyl and aryl;

provided that if -A-D- is —CH=CH—, then -A'-A- is other than —C($R_6$)=CH— and -D-D'- is other than

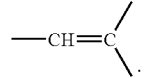

* * * * *